US00PP25380P3

(12) United States Plant Patent
Doguet et al.

(10) Patent No.: US PP25,380 P3
(45) Date of Patent: Mar. 24, 2015

(54) ZOYSIAGRASS PLANT NAMED 'LR1'

(50) Latin Name: ***Zoysia japonica* (L.) Merr.**
Varietal Denomination: LR1

(71) Applicants: David Doguet, Pleasanton, TX (US); Virginia Lehman, Lebanon, OR (US)

(72) Inventors: David Doguet, Pleasanton, TX (US); Virginia Lehman, Lebanon, OR (US)

( * ) Notice: Subject to any disclaimer, the term of this patent is extended or adjusted under 35 U.S.C. 154(b) by 138 days.

(21) Appl. No.: 13/986,673

(22) Filed: May 23, 2013

(65) Prior Publication Data

US 2014/0352016 P1 Nov. 27, 2014

(51) Int. Cl.
*A01H 5/00* (2006.01)

(52) U.S. Cl.
USPC ..... Plt./390

(58) Field of Classification Search
USPC ..... Plt./390
See application file for complete search history.

*Primary Examiner* — Annette Para

(57) ABSTRACT

An asexually reproduced variety of perennial zoysiagrass with a unique combination of morphological characters including medium leaf blade width, low canopy height, and medium stiff leaf texture.

2 Drawing Sheets

Latin name of the genus and species of the plant claimed: The present invention relates to the genus and species *Zoysia japonica* (L.) Merr.

Variety denomination: 'LR1'.

CROSS-REFERENCE TO RELATED APPLICATIONS

"Not Applicable"

STATEMENT REGARDING FEDERALLY SPONSORED RESEARCH OR DEVELOPMENT

"Not Applicable"

REFERENCE TO MICROFICHE APPENDIX

"Not Applicable"

BACKGROUND OF THE INVENTION

Field of Invention

The present invention relates to a new and distinct asexually reproduced variety of perennial zoysiagrass (*Zoysia japonica* (L.)) Merr.

BRIEF SUMMARY OF THE INVENTION

Background of the Invention

This invention relates to a new and distinct perennial zoysiagrass cultivar identified as 'LR1' zoysiagrass (herein referred to as 'LR1'). The inventors, David L. Doguet and Virginia G. Lehman, discovered 'LR1' under cultivated conditions near Poteet, Tex. in a collection of seedling plants originating from field grown open pollinated crosses between 'VJay' (unpatented), '6136' (U.S. Plant Pat. No. 17,808), and 'JaMur' (U.S. Plant Pat. No. 13,178) *zoysia* plants. 'LR1' was identified in 2005 as a distinctly different vegetative patch or clonal plant differing from the surrounding plants in a medium leaf texture, sparse flowering, low natural crown height, short internode lengths and a rapid lateral growth rate. The inventors asexually reproduced 'LR1' by taking vegetative cuttings of stolons and rhizomes, cutting the rhizomes and stolons into segments, each with a vegetative bud, and rooting them in potting media.

For purposes of registration under the "International Convention for the Protection of New Varieties of Plants" (generally known by its French acronym as the UPOV Convention) and noting Section 1612 of the Manual of Plant Examining Procedure, it is proposed that the title of the invention is Zoysiagrass plant named 'LR1'.

BRIEF DESCRIPTIONS OF THE ILLUSTRATIONS

FIG. 1. Tiller of 'LR1' zoysiagrass.
FIG. 2. Inflorescence of 'LR1' zoysiagrass.

COMPLETE DESCRIPTION OF THE VARIETY

'LR1' was characterized in greenhouse and field conditions. 'LR1' is a unique variety of zoysiagrass (*Zoysia japonica* (L.)) Merr. that was discovered under cultivated conditions. The inventors, David L. Doguet and Virginia G. Lehman, discovered 'LR1' under cultivated conditions near Poteet, Tex. in a collection of seedling plants originating from field grown open pollinated crosses between 'VJay' (unpatented), '6136' (U.S. Plant Pat. No. 17,808), and 'JaMur' (U.S. Plant Pat. No. 13,178) *zoysia* plants. 'LR1' was identified in 2005 as a distinctly different vegetative patch or clonal plant differing from the surrounding plants in a medium leaf texture, sparse flowering, low natural crown height, short internode lengths and a rapid lateral growth rate. The plants were located in USDA Plant Hardiness Zone 8. The inventors asexually reproduced 'LR1' by taking vegetative cuttings of stolons and rhizomes, cutting the rhizomes and stolons into segments, each with a vegetative bud, and rooting them in potting media. Planting of the rooted material provided planting stock for studying performance and for comparison of morphological characters after propagation. 'LR1' has been propagated by rhizomes, stolons, tillers, and sod. Asexually reproduced plants of 'LR1' have remained stable and true to type through successive generations of propagation. No seedling establishment from 'LR1' has been noticed in either greenhouse or field studies.

'LR1' is a perennial zoysiagrass that spreads by both stolons and rhizomes. Characteristics of 'LR1' measured in 2013 were taken from plants that were approximately 12 months in age. The greenhouse was located near Lebanon, Oreg., with a nighttime low temperature of 50 degrees F., and daytime high of 80 degrees F., and a minimum soil temperature of 77 degrees F. The plants were grown with a minimum 14-hour day length, supplemented with photosynthetically active radiation equivalent to approximately 50% sunlight. The plants were fertilized with the equivalent of 1 pound of actual N per month, using a soluble fertilizer of 20-20-20 in two equal soluble applications per month.

'LR1' has a medium leaf texture with a wider leaf than 'LR2', 'Cavalier' and 'Zorro' (Table 1). 'LR1' has an absence of leaf hairs versus 'Palisades', 'Zorro', 'Crowne', and 'Cavalier' which each have many leaf surface hairs (Table 2). 'LR1' has a thicker youngest stolon node and longer 1-2 stolon internode lengths than 'Diamond' (Table 3). 'LR1' has thicker stolon nodes than 'Zorro' or 'LR2' (Table 3). 'LR1' has a shorter unmown canopy height than 'Cavalier' or 'Zorro' (Table 4), and has a distinctive leaf height as a percentage of total canopy height that includes inflorescence height. The leaf height of 'LR1' is only 75% of the total canopy height, whereas the leaf length of 'Cavalier' extends beyond the inflorescence height. In addition, 'LR1' has an adaxial leaf color of 136 B (The R.H.S. Colour Chart), showing more blue in the genetic leaf coloration.

'LR1' has not shown susceptibility to the zoysiagrass mite when tested at Poteet, Tex., where susceptible varieties have shown the coachwhip leaf symptoms of the mite. 'LR1' has shown good turfgrass performance and temperature adaptation when tested as far north as Athens, Ga., USDA hardiness zone 8a, which would extend the area of adaptation for 'LR1' in a line from northern Georgia across central Texas in an East/West line and on a North/South line from Atlanta, south through Mexico. 'LR1' will be limited only by winter survival in colder regions. 'LR1' is similar to most medium textured zoysiagrasses in water use demands as shown in test situations near Poteet, Tex., 'LR1' is adapted from sandy to heavier loam soil textures and from slightly acid to slightly alkaline soil pH.

TABLE 1

Leaf blade widths and lengths and texture class of selected zoysiagrass cultivars, measured under greenhouse conditions in Lebanon, OR, 2012-2013.

| Variety | Leaf Stiffness | Length, 2nd youngest crown leaf --cm-- | Width, 2nd youngest crown leaf --mm-- | Leaf Texture Class |
|---|---|---|---|---|
| 'LR1' | Medium Stiff | 3.67 | 3.27 | Medium |
| 'LR2' | Medium Stiff | 2.96 | 2.61 | Medium |
| 'L1F' | Very Soft | 3.02 | 1.60 | Medium Fine |
| 'Diamond' | Soft | 2.50 | 1.40 | Very Fine |
| 'Cavalier' | Medium Stiff | 3.78 | 1.94 | Medium Fine |
| Zorro | Medium Stiff | 4.30 | 1.74 | Medium-Coarse |
| Lsd, p = 0.05 | | 1.03 | 0.24 | |

TABLE 2

Adaxial leaf hair presence or absence of selected zoysiagrass cultivars, measured under greenhouse conditions in Lebanon, OR, 2012-2013.

| Variety | Leaf hair, adaxial Presence/ Number |
|---|---|
| 'LR1' | Absent |
| 'Palisades' | Many |
| 'Zorro' | Many |
| 'Diamond' | Absent |
| 'Royal' | Absent |
| 'Crowne' | Many |
| 'Cavalier' | Many |

TABLE 3

Stolon characters of selected zoysiagrass cultivars, measured under greenhouse conditions in Lebanon, OR, 2012-2013.

| Variety | Thickness 1st youngest stolon node -mm- | Thickness 2nd youngest stolon node -mm- | Stolon Internode length, 1st to 2nd node -cm- | Stolon Internode length, 2nd to 3rd node -cm- | Stolon Internode length, 3rd to 4th node -cm- |
|---|---|---|---|---|---|
| 'LR1' | 2.42 | 2.20 | 1.36 | 1.44 | 1.24 |
| 'LR2' | 1.93 | 1.89 | 0.89 | 0.91 | 0.90 |
| 'Cavalier' | 1.65 | 1.57 | 1.22 | 1.38 | 1.38 |
| 'Diamond' | 1.44 | 1.49 | 1.0 | 0.94 | 1.86 |
| 'Zorro' | 1.57 | 1.67 | 1.51 | 1.47 | 1.45 |
| Lsd, p = 0.05 | 0.16 | 0.38 | 0.34 | 0.28 | 0.31 |

TABLE 4

Leaf and canopy characters of selected zoysiagrass cultivars, measured under greenhouse conditions in Lebanon, OR, 2012-2013.

| Variety | Canopy height --cm-- | Width, 4th youngest crown leaf --mm-- | Leaf Height as % Total Height --%-- |
|---|---|---|---|
| 'LR1' | 6.62 | 2.69 | 75 |
| 'LR2' | 7.32 | 2.18 | 66 |
| 'L1F' | 7.01 | 1.49 | 115 |
| 'Diamond' | 7.24 | 1.15 | |
| 'Cavalier' | 10.8 | 1.55 | 115 |
| 'Zorro' | 11.09 | 1.41 | 95 |
| Lsd, p = 0.05 | 1.76 | 0.71 | |

COMPLETE BOTANICAL DESCRIPTION OF THE VARIETY

Origin: 'LR1' is a cultivar of a single clone discovered under cultivated conditions in a Poteet, Tex. planting of zoysiagrass clones derived from a collection of seedling plants originating from field grown open pollinated crosses between 'VJay' (unpatented), '6136' (U.S. Plant Pat. No. 17,808), and 'JaMur' (U.S. Plant Pat. No. 13,178) *zoysia* plants.

Classification: *Zoysia japonica* (L.) Merr.

Growth habit: 'LR1' is a perennial plant that spreads by stolons and rhizomes and produces a dense, medium textured turfgrass. The inflorescence of 'LR1' is a terminal spike-like raceme, with spikelets on short pedicels.

Leaf blade: Rolled in the bud, flat surface.

Leaf blade pubescence: No hairs on abaxial or adaxial leaf.

Leaf sheath pubescence: Absent except for long hairs at mouth of sheath.

*'LR1' mean length sheath mouth hairs.*—1.7 mm; Diamond 1.0 mm.

Leaf blade margin: 'LR1=slight roughness; BM230=rough; Cavalier=mostly smooth.

Leaf blade veins: Obscure.

Leaf blade flexibility (softness): Medium stiff.

Vegetative leaf, 2nd youngest vegetative leaf:

*Blade length range.*—'LR1': 3.0 cm to 4.2 cm, mean length: 3.7 cm.

*Blade width mean.*—'LR1: 3.1 mm to 4.2 mm, mean width: 3.3 mm; 'Zorro' mean width: 1.74 mm; 'Diamond' mean width: 1.4 mm.

Sheath length, $4^{th}$ youngest vegetative leaf:

*Mean length 'LR1'.*—2.2 cm; 'Diamond' mean length: 2.93 cm.

Stolon leaf angle, third youngest leaf: 'LR1': 73; 'Cavalier': 76; 'Diamond': 52.

Inflorescence characters:

*Culm total length, including floral area to node below flag leaf.*—7.2 cm. Length of stem of inflorescence: 5.5 cm. Floral area length: 1.7 cm.

*Culm width, stem thickness, base of floral area.*—1.0 mm.

*Anther length.*—1.3 mm.

*Floret (seed) length.*—2.2 mm.

*Floret (seed) width.*—1.0 mm.

*Node thickness, node below flag leaf.*—1.0. mm.

*Pedicel length.*—1.5 mm.

*Flag leaf length.*—'LR1': 1.3 cm.

*Flag leaf width.*—'LR1': 1.4 mm.

Mature plant height, including inflorescence: 5.5 to 11.8 with a mean of 8.1 cm.

Color notations, vegetative characters, based on The R.H.S. Colour Chart (light quality, photoperiod, and general growth of the plants affect color notations):

*Leaf blade color adaxial leaf surface.*—136 B green.

*Leaf blade color abaxial leaf surface.*—137A green.

*Stolon color.*—158A to 158C yellow-white, 164 D greyed orange.

Color notations, floral characters, based on The R.H.S. Colour Chart (light quality, photoperiod, and general growth of the plants affect color notations):

*Culm stalk.*—144A yellow green.

*Stigma.*—155B, 160C greyed yellow.

*Anther color, fresh.*—155 B, 160C greyed yellow.

*Anthers, mature, dried.*—164C, 164D greyed orange.

Turf quality (rated 1-9, 9 best): 'LR1': 7; 'Meyer': 5.

References Cited
U.S. Patent Documents

| | | | |
|---|---|---|---|
| November 2002 | Doguet, D. | U.S. PP 13,178. | 'JaMur' zoysiagrass |
| June 2007 | Doguet, D. | U.S. PP 17,808. | '6136' zoysiagrass |
| July 1997 | Engelke, M.C. | U.S. PP 10,778. | 'Cavalier' zoysiagrass |
| October 1998 | Engelke, M.C. | U.S. PP 10,636. | 'Diamond' zoysiagrass |
| October 2000 | Engelke, M.C. | U.S. PP 11,570. | 'Crowne' zoysiagrass |
| September 2000 | Engelke, M.C. | U.S. PP 11,515. | 'Palisades' zoysiagrass |
| July 2002 | Engelke, M.C. | U.S. PP 14,130. | 'Zorro' zoysiagrass |

We claim:

1. A new and distinct variety of zoysiagrass plant, substantially as described and illustrated herein, characterized particularly by a unique combination of morphological characters.

* * * * *

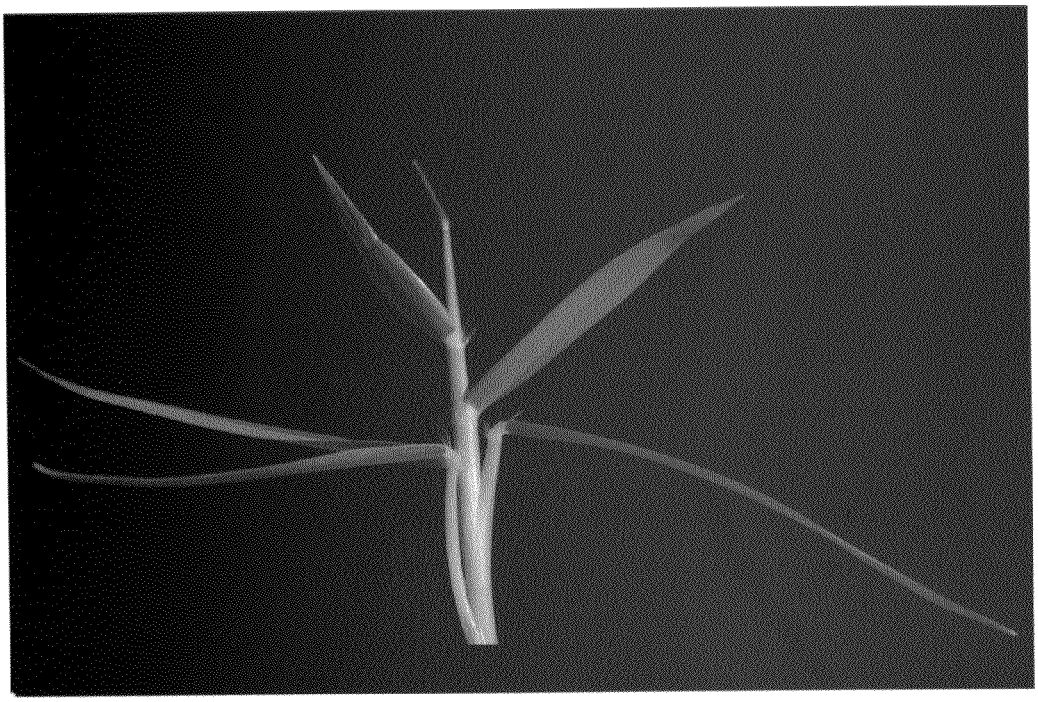
Figure 1. Tiller of 'LR1' zoysiagrass.

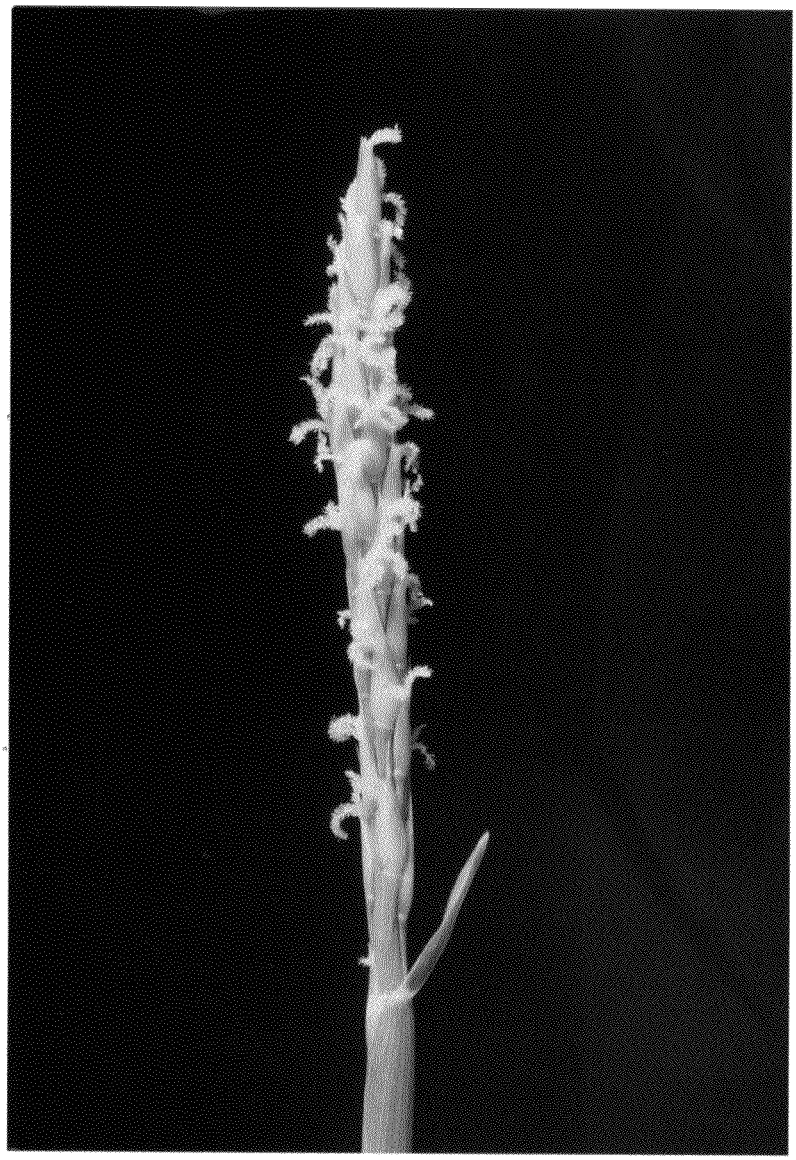
Figure 2. Inflorescence of 'LR1' zoysiagrass.